(12) United States Patent
Borthakur

(10) Patent No.: US 7,399,889 B2
(45) Date of Patent: Jul. 15, 2008

(54) PROCESS FOR THE PREPARATION OF VANILLIN FROM AGRICULTURAL WASTE

(75) Inventor: Naleen Borthakur, Jorhat (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 11/705,611

(22) Filed: Feb. 12, 2007

(65) Prior Publication Data

US 2007/0270620 A1 Nov. 22, 2007

(30) Foreign Application Priority Data

Feb. 13, 2006 (IN) .......................... 382/DEL/2006

(51) Int. Cl.
*C07C 45/65* (2006.01)
*C07C 45/78* (2006.01)
(52) U.S. Cl. ...................... 568/435; 568/438
(58) Field of Classification Search ................. 568/435, 568/438
See application file for complete search history.

(56) References Cited

U.S. PATENT DOCUMENTS 6,372,461 B1 * 4/2002 Frost .......................... 435/156

OTHER PUBLICATIONS

Herrman et al. Methyltrioxorhenium: oxidative cleavage of CC-double bonds and its application in a highly efficient synthesis of vanillin from biological waste. Journal of Molecular Catalysis A: Chemical vol. 153 (2000), pp. 49-52.*

* cited by examiner

*Primary Examiner*—Sikarl A. Witherspoon
(74) *Attorney, Agent, or Firm*—Ladas & Parry LLP

(57) ABSTRACT

The present invention provides a process for the preparation of Vanillin (4-hydroxy-3-methoxy benzaldehyde) by a single-step oxidation of ferulate moiety of rice straw, a renewable agricultural waste. This is a chemical method where vanillin is produced from a renewable resource in a single-step using a green oxidizing reagent and green solvent. Apart from that the water and the inorganic compounds can be recycled.

21 Claims, No Drawings

PROCESS FOR THE PREPARATION OF VANILLIN FROM AGRICULTURAL WASTE

FIELD OF THE INVENTION

The present invention relates to a process for the preparation of Vanillin (4-hydroxy-3-methoxy benzaldehyde).

This invention particularly relates to a novel method for synthesis of vanillin. More particularly the present invention relates to chemical process for the preparation of vanillin by a single-step oxidation of ferulate moiety of rice straw, a renewable agricultural waste in the presence of hydrogen peroxide, manganese sulphate, cupric chloride, sodium acetate and sulphuric acid and water under reflux condition in 1-3 hours. The process does not involve any costly or hazardous chemicals.

BACKGROUND AND PRIOR ART OF THE INVENTION

Vanillin is a key additive to food products, perfumery, beverage and an intermediate in pharmaceutical industry. The world production of synthetic vanillin is estimated to be over 3000 tones per annum. With the current growth rate (5.75% annually) the global demand is likely to make an exponential growth. Vanillin is naturally obtained from *Vanilla planifolia* Andrew (*Orchidaceae*) pods. Vanilla flavour extracted from cured beans of the vanilla plant (*Vanilla planifolia* Andrew) is used as a flavouring agent in food and currently has high demand. The traditional method of production of natural vanillin is cumbersome as it involves cultivation of plants in restricted climatic regions, hand pollination with limited success and the tedious processes for curing and extraction of products from the beans. This 'natural' vanillin, can cover only 1% of the global demand and is costly (US$4,00.00-500.00 per kilogram) [*Virginia Commonwealth University News*, 14.04.2003, vcunews@vcu.edu]. It is estimated that even to cater to 5% of global demand of vanillin 2.39 Lakh hectare of land has to be brought under cultivation causing deforestation of huge tract of virgin forest [www.tidco.com/tidcodocs/tn/Opportunities/Vanillin.doc]. Apart from that natural calamity can cause havoc in vanilla cultivation. In 2001 a devastating hurricane in Madagascar the world's biggest vanilla producer destroyed about 35% of the crop and 15% of the stocks in storage, sky rocketing the price from US$20.00-US$40.00 to US$200.00-US$230.00 a kilogram [www.foodnavigator.com/newsnews-NG.asp].

The recent focus on vanillin production is centered on isolation of ferulic acid from agro-waste and its subsequent conversion to vanillin. Recently biotechnological approaches have been initiated to achieve this target. Some progress is being made in developed countries [P. Bonnarme, G. Ferm, A. Durand; *Ind. Perfumer*, 45(1), 63-67, 2001] to prepare vanillin through a biotechnological route from ferulate-moiety containing agricultural waste. Here ferulic acid is first isolated from its source, which is converted to vanillin and vanillic acid using microbes [Synthesis of vanillin from a carbon source; John W. Frost, U.S. Pat. No. 6,372,461 and references cited]. Use of glucose instead of ferulic acid as feed-stock results in microbial conversion to vanillic acid. The latter is reduced to vanillin by an aryl-aldehyde dehydrogenase enzyme released from a genetically manipulated *E. coli* microbe [Synthesis of vanillin from a carbon source; John W. Frost, U.S. Pat. No. 6,372,461]. The biotechnological processes require multi-steps, heavy investment and stringent control to dictate the specific enzymes to work, and have high risk of mutation or inhibition of growth of microorganisms in presence of metabolites and are slow. Therefore, there is a scope to develop chemical methods that will be able to convert ferulate moiety of agricultural waste to vanillin in minimum chemical steps in an environmentally benign way.

Any new process aimed at preparation of vanillin today must concern itself for use of renewable resources and environmentally-friendly chemicals and solvents. In this case the ideal raw material is ferulate moiety containing agro-wastes such as rice straw, which is cheap and abundant, hydrogen peroxide as the oxidizing agent and water as solvent.

The hitherto relevant known methods for preparation of vanillin are:

A reference may be made to the guaiacol method [Esposito L. et.al., "Vanillin" Kirk-Othmer Encyclopedia of Chemical Technology; Vol: 24, 812-814, 1997; Fourth Ed., Kroschwitz, J. I., Howe-Grant, M., Ed., Wiley: New York]

Vanillin is now industrially prepared in multi-steps using guaiacol as the starting material. Guaiacol itself is prepared from catechol. Catechol is prepared from phenol a crude-oil based chemical.

The drawback of the process is that it involves multi-steps and non-renewable crude oil based chemicals.

Another reference may be made to Vanillin from lignin [Esposito L. et.al., "Vanillin" Kirk-Othmer Encyclopedia of Chemical Technology; Vol: 24, 812-814, 1997; Fourth Ed., Kroschwitz, J. I., Howe-Grant, M., Ed., Wiley: New York]

This industrial method of preparation of vanillin is based on lignin as raw material. In this method lignin from cellulose industry is treated with alkali at elevated temperature in presence of oxidants. The vanillin formed is separated from by-products such as acetovanillin, 4-hydroxy-3-methoxy acetophenone and few other compounds.

The drawback of the process is that in spite of use of renewable lignin as raw material the process generates 160 tones of caustic wastes per ton of vanillin. This volume of waste is a threat to the environment.

Yet another reference may be made to Vanillin from ferulic acid [W. A. Herrmann, T. Weskamp, J. P. Zoller, R. W. Fischer; *J. Mol. Catal.*, 153, 49-52, 2000]

In this method trans-ferulic acid is converted to vanillin using hydrogen peroxide in presence of methyl trioxorhenium complex as catalyst.

The drawback of the method is that methyl trioxorhenium complex is costly and short-lived in presence of water. On the other hand commercial hydrogen peroxide (ca. 30%) contains water. The reaction has to be carried out in a good amount of water-trapping agent magnesium sulphate. The reaction can be carried out using methyl tributyl ether as solvent, which is toxic and expensive. Under such a stringent condition the reaction remains only of academic interest.

Yet another reference may be made to Vanillin from alkali lignin by green chemical method [Zhou Qiang; Chen Zhonghao; China Patent No. CN 1285395; 2001]

In this method vanillin is prepared from alkali lignin by catalytic oxidation reaction with recovery of catalyst and solvent.

The drawback of the method is that lignin has to be separated with alkali prior to the oxidation reaction resulting in multiple steps.

Yet another reference may be made to Vanillin from alkali lignin by nitrobenzene oxidation method [Kozlov I. A., Kuznetsov B. N., Gogotov A. F., Rybal Chenko T. So Ran; Russian patent No. RU2179968, 2002] In this method lignin is oxidized by alkaline nitrobenzene.

The drawback of the method is that it uses nitrobenzene a toxic compound and the method also produces syringaldehyde as the major product.

Considering the environment-polluting non-renewable petroleum crude based chemicals employed in the existing methods there is a great scope for inventing environmentally-friendly chemical processes that can use renewable raw materials for the synthesis of vanillin. It is also important to recycle chemicals and solvents in one hand for optimum utilization and on the other to answer the demand of the environmental considerations. The use of renewable starting materials such as agrowastes do not demand extra virgin land and water for cultivation.

Hydroxycinnamic acids, particularly ferulic acid (4-hydroxy-3-methoxy cinnamic acid, occurs widely in the cell walls of *graminaceous* plants. All the cell walls of sugarcane and rice straw contain 5-15% hydroxycinnamic moieties based on total lignin. The conversion of ferulate (hydroxycinnamate) moiety into vanillin is of current global interest. But the interest is confined to biotechnological methods only. The biotechnological processes are slow, require heavy investment and stringent control to dictate the specific enzymes to work, and have high risk of mutation or inhibition of growth of microorganisms in presence of metabolites. Therefore, it is very much necessary to develop clean chemical methods to convert ferulates of agrowastes such as rice straw to vanillin eliminating the drawbacks of other methods cited above. The present invention answers all the above concerns by using rice straw as the renewable raw material, water as solvent and hydrogen peroxide as the oxidizing agent along with a catalyst and co-catalyst both of which are cheap, recyclable and stable in presence of water. The synthesis of vanillin can be done by this invention in a single simple step. All the chemicals and solvent can be recycled except hydrogen peroxide. Hydrogen peroxide is consumed in the reaction with release of water as the by-product.

OBJECTS OF THE INVENTION

The main objective of the present invention is to provide a process for the preparation of vanillin from rice straw which obviates the drawbacks of the hitherto known prior art as detailed above.

Another objective of the present invention is to provide a process for the preparation of vanillin by oxidation of ferulate moiety of rice straw, a renewable agricultural waste in the presence of hydrogen peroxide Yet another objective of the present invention is to provide a process for the preparation vanillin by using hydrogen peroxide a green oxidizing agent and water a green solvent that makes the process environmentally friendly.

Yet another objective of the present invention is to provide a process for the preparation of vanillin by recycling the water solution containing the inorganic compounds from an earlier experiment thereby reducing the cost of the chemicals and avoiding the release of the toxic inorganic chemicals to the environment.

SUMMARY OF THE INVENTION

Accordingly the present invention provides a process for the preparation of vanillin from agricultural waste which comprises reacting a ferulate containing renewable agrowaste with hydrogen peroxide in the presence of a catalyst selected from manganese acetate, manganese chloride, manganese nitrate and manganese sulphate and co-catalysts selected from salts of cobalt, nickel and copper, essentially with potassium and sodium salt, sodium acetate and mineral acid in water under reflux for a period in the range of 1-3 hours, cooling the above said reaction mixture to a temperature of about 25-30° C., separating the solid mass by filtration, followed by washing with water, collecting the washing along with filterate and extracting it with an organic solvent followed by washing the organic part with sodium bicarbonate and water, respectively and drying the resultant organic layer by known methods to obtain the desired product and reusing the aqueous layer for further reaction with agrowaste.

In an embodiment of the present invention, the organic solvent used is selected from the group consisting of dichloromethane, dichloroethane and ethyl acetate.

In another embodiment of the present invention, the mineral acid used is selected from the group consisting of sulphuric acid, hydrochloric acid, nitric acid and acetic acid. In another embodiment of the present invention, the salt of cobalt used is selected from the group consisting of cobalt chloride, cobalt acetate, cobalt sulphate and cobalt nitrate.

In yet another embodiment of the present invention, the salt of copper used is selected from the group consisting of cupric chloride, cupric sulphate, cupric nitrate and cupric acetate.

In yet another embodiment of the present invention, the salts of nickel used is selected from the group consisting of nickel chloride, nickel sulphate, nickel nitrate and nickel acetate.

In yet another embodiment of the present invention, the potassium salt used is potassium hydrogen sulphate and potassium acetate.

In yet another embodiment of the present invention, the sodium salt used is sodium hydrogen sulphate and sodium acetate.

In yet another embodiment of the present invention, the potassium salt preferably used is potassium hydrogen sulphate.

In yet another embodiment of the present invention, the sodium salt preferably used is sodium hydrogen sulphate.

In yet another embodiment of the present invention, the co-catalyst used is preferably cupric chloride dehydrate with sodium acetate and potassium bisulphate.

In yet another embodiment of the present invention, the amount of hydrogen peroxide used is about 10-15 ml of 50% $H_2O_2$ per 20 gm of agrowaste used.

In yet another embodiment of the present invention, the amount of manganese sulphate hydrate used is in the range of 1.0-1.5 mmole per 20 gm of agrowaste used. In yet another embodiment of the present invention, the amount of potassium salt used is in the range of 1.2-2.0 mmole per 20 gm of agrowaste used.

In yet another embodiment of the present invention, the amount of copper salt used is in the range of 0.2-0.3 mmole per 20 gm of agrowaste used.

In yet another embodiment of the present invention, the amount of sodium salt used is in the range of 1.2-2.0 mmole per 20 gm of agrowaste used.

In yet another embodiment of the present invention, the amount of mineral acid used is about 10 ml per 20 gm of agrowaste used.

In yet another embodiment of the present invention, the aqueous layer containing inorganics obtained is recyclable for further reaction with agrowaste in presence of hydrogen peroxide and sulfuric acid.

In yet another embodiment of the present invention, the hydrogen peroxide used is about 20 ml per 50 gm of agrowaste when aqueous layer containing inorganics is recycled.

In yet another embodiment of the present invention, the sulfuric acid used is about 5 ml per 50 gm of agrowaste when aqueous layer containing inorganics is recycled. In yet another embodiment of the present invention, the renewable agrowaste used is rice straw.

DETAILED DESCRIPTION OF THE INVENTION

Rice straw a renewable resource on reacting with hydrogen peroxide a green reagent, manganese sulphate, potassium bisulphate, cupric chloride, sodium acetate, sulphuric acid and water, a green solvent on heating produces vanillin in a single-step. This is the first ever method where vanillin is chemically produced from rice straw a renewable resource in a single-step. The single-step process reported in the invention is novel and non-obvious. Apart from that water the solvent and the inorganic compounds used in the process can be recycled which makes it environmentally friendly.

The following specific examples are given by way of illustration of the invention in actual practice and therefore should not be construed to limit the scope of the present invention.

EXAMPLE 1

Preparation of Rice Straw:

Dry rice straw 300 grams was cut in to small pieces (ca. 1 cm in length) and extracted with petroleum ether (60°-80° C.) in a Soxhlet apparatus to remove fats and coloring materials. This rice straw was preserved and used in subsequent experiments.

EXAMPLE 2

Conversion of Rice Straw to Vanillin:

Rice straw (20 grams), manganese sulphate hydrate ($MnSO_4$, $H_2O$, 200 mg, 1.18 mmol); potassium bisulphate ($KHSO_4$, 200 mg, 1.46 mmol); cupric chloride di hydrate ($CuCl_2$, $2H_2O$; 50 mg 0.29 mmol); sodium acetate tri hydrate (NaOAc, $3H_2O$, 200 mg, 1.46 mmol); sulphuric acid (conc.$H_2SO_4$, 10 ml); hydrogen peroxide ($H_2O_2$, 50%, 10 ml) and water (300 ml) were mixed and refluxed in a 500 ml round bottom flask for one hour. The reaction mixture was cooled, filtered to separate the straw, washed with 30 ml (10 ml, 3 times), washings collected with the filtrate. The filtrate was extracted with dichloromethane (30 ml). The organic part was washed with minimum amount of sodium bi-carbonate concentrated solution (3-5 ml), washed with minimum volume of water (3-5 ml). The organic layer was dried over anhydrous sodium sulphate, and vanillin content estimated (3.3 mg). Vanillyl alcohol and furfurel are also present [also in example 3 & 4].

EXAMPLE 3

Rice straw (50 grams), manganese sulphate hydrate ($MnSO_4$, $H_2O$, 500 mg, 2.95 mmol); potassium bisulphate ($KHSO_4$, 500 mg, 3.65 mmol); cupric chloride di hydrate ($CuCl_2$, $2H_2O$; 100 mg, 0.58 mmol); sodium acetate tri hydrate (NaOAc, $3H_2O$, 500 mg, 3.65 mmol); sulphuric acid (conc.$H_2SO_4$, 10 ml); hydrogen peroxide ($H_2O_2$, 50%, 25 ml) and water (500 ml) were refluxed together in a 1 liter round bottom flask for three hours. The reaction mixture was cooled, filtered to separate the straw, washed with 30 ml (10 ml, 3 times), washings collected with the filtrate. The filtrate was extracted with dichloromethane (40 ml). The organic part was washed with minimum amount of sodium bi-carbonate concentrated solution (3-5 ml), washed with minimum volume of water (3-5 ml). The organic layer was dried over anhydrous sodium sulphate, and vanillin content estimated (8.74 mg). Also, Vanillyl alcohol and furfurel present

EXAMPLE 4

Recycling of the Aqueous Solution Containing Inorganics from a Completed Experiment:

To rice straw (50 grams) the aqueous part (500 ml) of the experiment [example 2 after separation of vanillin i.e. extraction with dichloromethane] was added along with hydrogen peroxide (20 ml) and sulphuric acid (conc., 5 ml) and refluxed for three hours. The reaction mixture was cooled, filtered to separate the straw, washed with 30 ml (10 ml, 3 times), washing collected with the filtrate. The filtrate was extracted with dichloromethane (40 ml). The organic part was washed with minimum amount of sodium bi-carbonate concentrated solution (3-5 ml), washed with minimum volume of water (3-5 ml). The organic layer was dried over anhydrous sodium sulphate, and vanillin content estimated (4.3 mg). Also, Vannillyl alcohol and furfurel present.

EXAMPLE 5

Effect of Cupric Chloride

Rice straw (20 grams), manganese sulphate hydrate ($MnSO_4$, $H_2O$, 200 mg, 1.18 mmol); potassium bisulphate ($KHSO_4$, 200 mg, 1.46 mmol); sodium acetate tri hydrate (NaOAc, $3H_2O$, 200 mg, 1.46 mmol); sulphuric acid (conc.$H_2SO_4$, 10 ml); hydrogen peroxide ($H_2O_2$, 50%, 10 ml) and water (300 ml) were refluxed together in a 500 ml round bottom flask for one hour. The reaction mixture was cooled, filtered to separate the straw, washed with 30 ml (10 ml, 3 times), washing collected with the filtrate. The filtrate was extracted with dichloromethane (30 ml). The organic part was washed with minimum amount of sodium bi-carbonate concentrated solution (3-5 ml), washed with minimum volume of water (3-5 ml). The organic layer was dried over anhydrous sodium sulphate. Trace amount of vanillin formed (TLC, petroleum ether:ethyl acetate, 3.5:1.5, silica gel plate).

EXAMPLE 6

Effect of Potassium bi Sulphate

Rice straw (20 grams), manganese sulphate hydrate ($MnSO_4$, $H_2O$, 200 mg, 1.18 mmol); cupric chloride di hydrate ($CuCl_2$, $2H_2O$; 50 mg, 0.29 mmol); sodium acetate tri hydrate (NaOAc, $3H_2O$, 200 mg, 1.46 mmol); sulphuric acid (conc.$H_2SO_4$, 10 ml); hydrogen peroxide ($H_2O_2$, 50%, 10 ml) and water (300 ml) were refluxed together in a 500 ml round bottom flask for one hour. The reaction mixture was cooled, filtered to separate the straw, washed with 30 ml (10 ml, 3 times), washing collected with the filtrate. The filtrate was extracted with dichloromethane (30 ml). The organic part was washed with minimum amount of sodium bi-carbonate concentrated solution (3-5 ml), washed with minimum volume of water (3-5 ml). The organic layer was dried over anhydrous sodium sulphate. Trace amount of vanillin formed (TLC, petroleum ether:ethyl acetate, 3.5:1.5, silica gel plate).

EXAMPLE 7

Effect of Temperature

Rice straw (20 grams), manganese sulphate hydrate ($MnSO_4$, $H_2O$, 200 mg, 1.18 mmol); potassium bisulphate ($KHSO_4$, 200 mg, 1.46 mmol); cupric chloride di hydrate ($CuCl_2$, $2H_2O$; 50 mg, 0.29 mmol); sodium acetate tri hydrate (NaOAc, $3H_2O$, 200 mg, 1.46 mmol); sulphuric acid (conc.$H_2SO_4$, 10 ml); hydrogen peroxide ($H_2O_2$, 50%, 10 ml)

and water (300 ml) were stirred together at 25° C. with a mechanical stirrer in a 500 ml round bottom flask for three hours. The reaction mixture was cooled, filtered to separate the straw, washed with 30 ml (10 ml, 3 times), washing collected with the filtrate. The filtrate was extracted with dichloromethane (30 ml). The organic part was washed with minimum amount of sodium bicarbonate concentrated solution (3-5 ml), washed with minimum volume of water (3-5 ml). The organic layer was dried over anhydrous sodium sulphate. TLC showed no formation of vanillin.

Advantages of the Invention
1. Agro-waste such as rice straw produces vanillin in a single-step.
2. Unlike current methods no prior separation of lignin from cellulose is required for vanillin preparation.
3. The chemicals used are cheap and commercially available.
4. Green reagent hydrogen peroxide and green solvent water are used
5. The inorganic compounds can be recycled.
6. Water, the solvent, can be recycled
   The method is eco-friendly
   The invention claimed is:

1. A process for the preparation of vanillin from agricultural waste which comprises reacting a ferulate containing renewable agro-waste with hydrogen peroxide in the presence of a catalyst selected from manganese acetate, manganese chloride, manganese nitrate and manganese sulphate and co-catalysts selected from salts of cobalt, nickel and copper, essentially with potassium and sodium salt, sodium acetate and mineral acid or acetic acid in water under reflux for a period in the range of 1-3 hours, cooling the above said reaction mixture to a temperature of about 25-300° C., separating the solid mass by filtration, followed by washing with water, collecting the washing along with filterate and extracting it with an organic solvent followed by washing the organic part with sodium bi-carbonate and water, respectively and drying the resultant organic layer by known methods to obtain the desired product and reusing the aqueous layer for further reaction with agrowaste.

2. The process according to claim 1, wherein the organic solvent used is selected from the group consisting of dichloromethane, dichloroethane and ethyl acetate.

3. The process according to claim 1, wherein mineral acid used is selected from the group consisting of sulphuric acid, hydrochloric acid, nitric acid and acetic acid.

4. The process according to claim 1, wherein the salt of cobalt used is selected from the group consisting of cobalt chloride, cobalt acetate, cobalt sulphate and cobalt nitrate.

5. The process according to claim 1, wherein the salt of copper used is selected from the group consisting of cupric chloride, cupric sulphate, cupric nitrate and cupric acetate.

6. The process according to claim 1, wherein the salt of nickel used is selected from the group consisting of nickel chloride, nickel sulphate, nickel nitrate and nickel acetate.

7. The process according to claim 1, wherein the potassium salt used is selected from the group consisting of potassium hydrogen sulphate and potassium acetate.

8. The process according to claim 1, wherein the sodium salt used is selected from the group consisting of sodium hydrogen sulphate and sodium acetate.

9. The process according to claim 7, wherein the potassium salt preferably used is potassium hydrogen sulphate.

10. The process according to claim 8, wherein the sodium salt preferably used is sodium hydrogen sulphate.

11. The process according to claim 1, wherein the co-catalysts used are preferably cupric chloride dehydrate, sodium acetate and potassium bisulphate.

12. The process according to claim 1, wherein the amount of hydrogen peroxide used is about 10-15 ml of 50% $H_2O_2$ per 20 gm of agrowaste used.

13. The process according to claim 1, wherein the amount of manganese sulphate hydrate used is in the range of 1.0-1.5 mmole per 20 gm of agrowaste used.

14. The process according to claim 1, wherein the amount of potassium salt used is in the range of 1.2-2.0 mmole per 20 gm of agrowaste used.

15. The process according to claim 1, wherein the amount of copper salt used is in the range of 0.2-0.3 mmole per 20 gm of agrowaste used.

16. The process according to claim 1, wherein the amount of sodium salt used is in the range of 1.2-2.0 mmole per 20 gm of agrowaste used.

17. The process according to claim 1, wherein the amount of mineral acid used is about 10 ml per 20 gm of agrowaste used.

18. The process according to claim 1, wherein the aqueous layer containing inorganics obtained is recyclable for further reaction with agrowaste in presence of hydrogen peroxide and sulfuric acid.

19. The process according to claim 1, wherein the hydrogen peroxide used is about 20 ml per 50 gm of agrowaste when aqueous layer containing inorganics is recycled.

20. The process according to claim 1 wherein the mineral acid is sulfuric acid and is used at about 5 ml per gm of agrowaste when the aqueous layer containing inorganics is recycled.

21. The process according to claim 1, wherein the renewable agrowaste used is rice straw.

* * * * *